(12) United States Patent
Raju et al.

(10) Patent No.: US 12,295,740 B2
(45) Date of Patent: May 13, 2025

(54) ULTRASOUND-BASED CLOSED-LOOP CONTROL OF PATIENT THERAPY

(71) Applicant: KONINKLIJKE PHILIPS N.V., Eindhoven (NL)

(72) Inventors: Balasundar Iyyavu Raju, North Andover, MA (US); Mckee Dunn Poland, Andover, MA (US); Ivan Salgo, Pelham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 576 days.

(21) Appl. No.: 17/420,998

(22) PCT Filed: Dec. 30, 2019

(86) PCT No.: PCT/EP2019/087127
§ 371 (c)(1),
(2) Date: Jul. 6, 2021

(87) PCT Pub. No.: WO2020/144075
PCT Pub. Date: Jul. 16, 2020

(65) Prior Publication Data
US 2022/0079516 A1  Mar. 17, 2022

Related U.S. Application Data

(60) Provisional application No. 62/789,134, filed on Jan. 7, 2019.

(51) Int. Cl.
*A61B 5/00* (2006.01)
*A61B 8/08* (2006.01)
(Continued)

(52) U.S. Cl.
CPC .......... *A61B 5/4836* (2013.01); *A61B 5/6801* (2013.01); *A61B 5/742* (2013.01);
(Continued)

(58) Field of Classification Search
CPC ..... A61B 5/4836; A61B 5/6801; A61B 5/742; A61B 5/746; A61B 5/7282; A61B 8/08; A61B 8/5223; G16H 40/63
See application file for complete search history.

(56) References Cited

U.S. PATENT DOCUMENTS 8,870,797 B2  10/2014  Paradis
10,722,209 B2  7/2020  Chen
(Continued)

FOREIGN PATENT DOCUMENTS

WO  2016156446 A1  10/2016
WO  2017060871 A1  4/2017
WO  2018031714 A1  2/2018

OTHER PUBLICATIONS

International Search Report and Written Opinion of PCT/EP2019/087127, dated Apr. 7, 2020.
(Continued)

*Primary Examiner* — Amelie R Davis

(57) ABSTRACT

A system includes a transducer array configured to obtain ultrasound data of a subject; a processor in communication with the transducer array and a therapeutic device configured to deliver a therapy to the subject, wherein the processor is configured to: receive the ultrasound data; identify an anatomical feature of the subject using the ultrasound data; compute a measure associated with the anatomical feature; determine if the measure satisfies a threshold; determine a change in an operating status of the therapeutic device based on if the measure satisfies the threshold; and output, to the therapeutic device, a control signal representative of the change in the operating status. Associated methods, devices, and systems are also provided.

21 Claims, 4 Drawing Sheets

(51) Int. Cl.
 *G16H 40/63* (2018.01)
 *A61B 8/00* (2006.01)
(52) U.S. Cl.
 CPC ............ *A61B 5/746* (2013.01); *G16H 40/63* (2018.01); *A61B 5/7282* (2013.01); *A61B 8/08* (2013.01); *A61B 8/5223* (2013.01)

(56) References Cited

U.S. PATENT DOCUMENTS

| | | |
|---|---|---|
| 2010/0076315 A1 | 3/2010 | Erkamp |
| 2014/0366878 A1 | 12/2014 | Baron |
| 2017/0281938 A1* | 10/2017 | Creasey ............. A61N 1/36007 |
| 2018/0078754 A1* | 3/2018 | Perez .................. A61B 5/4848 |
| 2019/0167188 A1* | 6/2019 | Gifford, III ............. A61B 8/12 |
| 2020/0043602 A1 | 2/2020 | Kim |

OTHER PUBLICATIONS

Otani, Kyoko et al "Three-Dimensional Echocardiographic Assessment of Left Heart Chamber Size and Function with Fully Automated Quantification Software in Patients with Atrial Fibrillation", Journal of the American Society of Echocardiography, Oct. 2016.
Jiang, Chuan et al "Use of Lung Ultrasonography to Determine the Accuracy of Clinically Estimated Dry Weight in Chronic Hemodialysis Patients", International Urology and Nephrology, vol. 49, No. 12, Oct. 2017, pp. 2223-2230.

* cited by examiner

ULTRASOUND-BASED CLOSED-LOOP CONTROL OF PATIENT THERAPY

CROSS-REFERENCE TO PRIOR APPLICATIONS

This application is the U.S. National Phase application under 35 U.S.C. § 371 of International Application No. PCT/EP2019/087127, filed on Dec. 30, 2019, which claims the benefit of U.S. Provisional Patent Application Ser. No. 62/789,134, filed Jan. 7, 2019. These applications are hereby incorporated by reference herein.

TECHNICAL FIELD

The present disclosure relates generally to a controller that communicates with an ultrasound system and a therapeutic system delivering therapy to a patient. The controller provides closed loop control for the therapeutic system by monitoring the effect of therapy on the patient based on ultrasound data from the ultrasound system and changing the operation of the therapeutic system in response.

BACKGROUND

A variety of conventional therapeutic devices are meant to operate continuously, yet require a person to monitor the device operation in order to change settings or troubleshoot a problem. For example, dialysis machines, ventilators, and infusion devices operate with an open loop control system, leading to sub-optimal therapies. The open loop control system acts completely on the basis of input settings manually entered by a clinician. Any output data has no effect on how the therapeutic device operates. For example, a dialysis machine may be set to operate for a few hours without knowledge of how well the procedure is proceeding for a given patient. The patient may be weighed before and after dialysis. These manual steps may not be the most accurate assessment of how the procedure is going because little to no during-procedure monitoring is occurring. In some cases, a clinician must actively monitor a patient's vital signs before adjusting fluid infusion or medication administration. Such steps require the clinician's time and adversely affect the workflow efficiency of therapeutic procedures.

SUMMARY

Aspects of the present disclosure advantageously provide a closed loop control system for a therapeutic device using ultrasound data. The therapeutic device, such as a dialysis machine, ventilator, or infusion system, delivers a therapy to a patient. While the patient is receiving the therapy, an ultrasound probe obtains ultrasound data of a portion of the patient's anatomy that is related by the therapy. A computer processor automatically extracts from the ultrasound data, such as an ultrasound image of the anatomy, a measure representative of the effect the therapy is having on the patient. In some instances, the measure can be a numerical value, such as a diameter or volume, of the patient's anatomy. The measure is compared to a threshold that represents, for example, the desired outcome of the therapy. Depending the comparison, the computer processor can send a control signal to the therapeutic device to change its status. For example, if the comparison between the measure and threshold indicates that the desired outcome has been reached, then the computer processor can send a control signal to stop the therapy. If the comparison indicates that the patient is not responding to the therapy, the computer processor can send a signal to the therapeutic device to increase its operation (e.g., increase the amount of medication delivered to the patient by the infusion system).

The closed loop control system advantageously delivers automatically optimized therapy for the patient, which improves patient care. For example, the controller can change the function of the therapeutic device based on how the patient's anatomy is responding to therapy. The ultrasound image of the patient's anatomy allows for automatic determination of the patient's response to the therapy. Efficiency of the therapeutic workflow is advantageously improved by eliminating or minimizing the need for doctors and nurses to manually monitor therapy progress and manually change settings of the therapeutic device.

According to an exemplary embodiment, a system is provided. The system includes a transducer array configured to obtain ultrasound data of a subject; a processor in communication with the transducer array and a therapeutic device configured to deliver a therapy to the subject, wherein the processor is configured to: receive the ultrasound data; identify an anatomical feature of the subject using the ultrasound data; compute a measure associated with the anatomical feature; determine if the measure satisfies a threshold; determine a change in an operating status of the therapeutic device based on if the measure satisfies the threshold; and output, to the therapeutic device, a control signal representative of the change in the operating status.

In some embodiments, the operating status of the therapeutic device comprises an on/off status of the therapeutic device; and the change in the operating status comprises turning the therapeutic device on or off. In some embodiments, the operating status of the therapeutic device comprises an adjustable parameter of the therapeutic device; and the change in the operating status comprises an increase or a decrease in a value of the adjustable parameter. In some embodiments, the processor identifying the anatomical feature of the subject comprises: identifying an attribute of the ultrasound data representative of the anatomical feature. In some embodiments, the anatomical feature is a pulmonary edema; the attribute of the ultrasound data comprises B-lines; and the measure comprises a quantity of the B-lines. In some embodiments, the anatomical feature comprises an inferior vena cava; and the measure comprises a diameter of the inferior vena cava. In some embodiments, the anatomical feature comprises at least one of a right ventricle or a left ventricle; and the measure comprises a volume of at least one of the right ventricle or the left ventricle. In some embodiments, wherein the therapeutic device comprises at least one of a dialysis machine, an infusion device, or a ventilator. In some embodiments, the processor is configured to determine if the measure is outside of a predefined criteria; and output an alert to a user based on determining if the measure is outside of the predefined criteria. In come embodiments, the processor is in communication with a display; and the processor outputting the alert comprises providing a graphical representation of the alert to the display. In some embodiments, the processor is configured to receive therapy data from the therapeutic device; and the processor determining the change in the operating status of the therapeutic device is further based on the therapy data. In some embodiments, the processor is in communication with a vital sign monitoring device; the processor is configured to receive vital sign data from the vital sign monitoring device; and the processor determining the change in the operating status of the therapeutic device is further based on the vital sign data. In some embodiments, the system further comprises at least one of a transthoracic echocardiography (TTE) probe, a transesophageal echocardiography probe (TEE), or a wearable patch, wherein the transducer array is coupled to at least one of the TTE probe, the TEE probe, or the wearable patch.

According to an exemplary embodiment, a method is provided. The method includes receiving ultrasound data of a subject obtained by a transducer array; identifying, by a processor in communication with the transducer array, an anatomical feature of the subject using the ultrasound data; computing, by the processor, a measure associated with the anatomical feature; determining, by the processor, if the measure satisfies a threshold; determining, by the processor, a change in an operating status of a therapeutic device based on if the measure satisfies the threshold, wherein the therapeutic device delivers a therapy to the subject; and outputting, by the processor, a control signal representative of the change in the operating status to the therapeutic device.

In some embodiments, the operating status of the therapeutic device comprises an on/off status of the therapeutic device; and determining the change comprises turning the therapeutic device on or off. In some embodiments, the operating status of the therapeutic device comprises an adjustable parameter of the therapeutic device; and determining the change comprises increasing or decreasing a value of the adjustable parameter. In some embodiments, identifying the anatomical feature of the subject comprises identifying an attribute of the ultrasound data representative of the anatomical feature. In some embodiments, the method further includes: determining if the measure is outside of a predefined criteria; and outputting an alert to a user based on determining if the measure is outside of the predefined criteria. In some embodiments, the method further includes: receiving therapy data from the therapeutic device, wherein determining the change in the operating status of the therapeutic device is further based on the therapy data. In some embodiments, the method further includes: receiving vital sign data of the subject from a vital sign monitoring device; wherein determining the change in the operating status of the therapeutic device is further based on the vital sign data.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
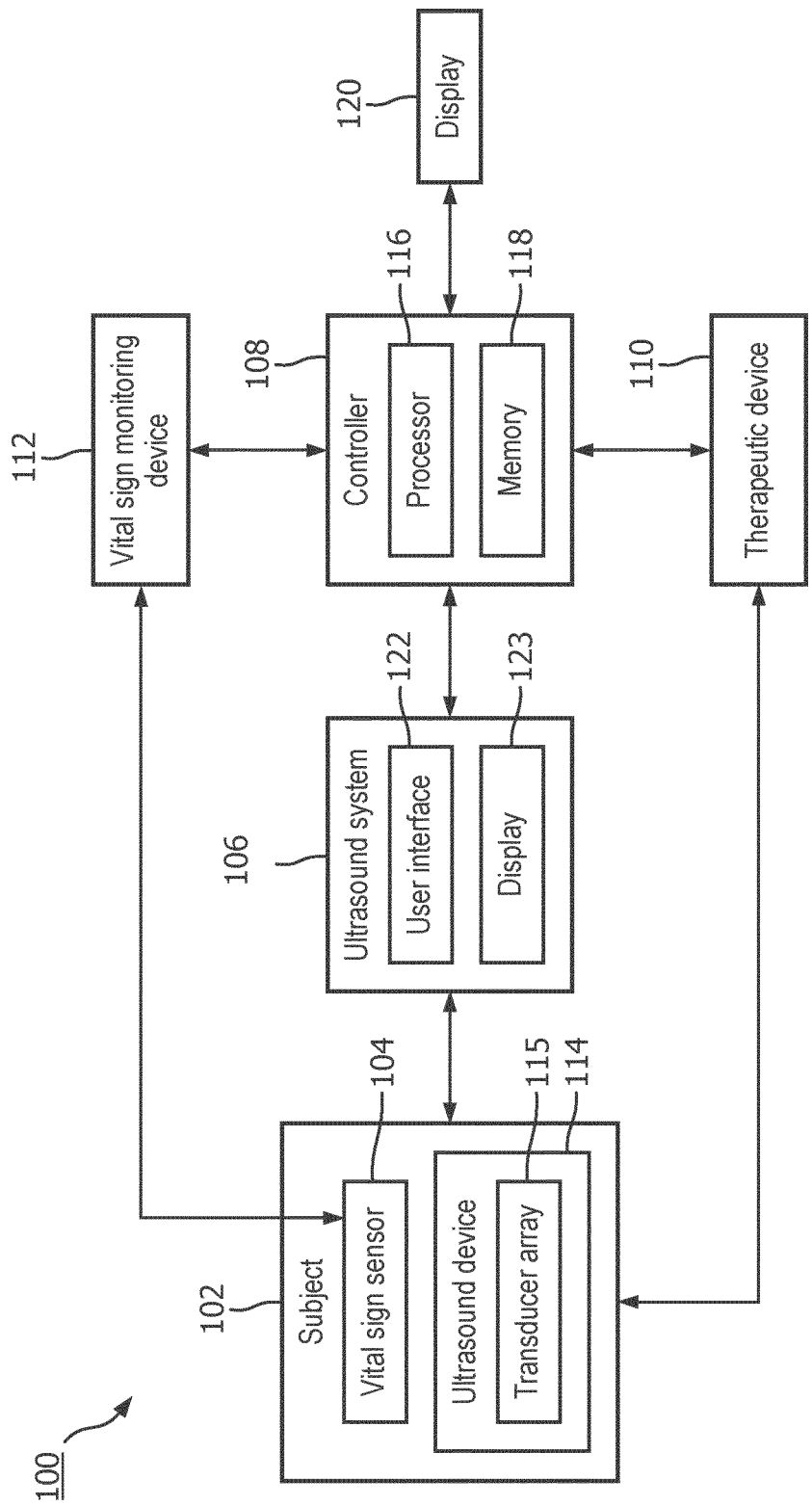
FIG. 1 is a block diagram of a system for closed loop control of a therapeutic device using ultrasound data, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a block diagram of a system 100, according to aspects of the present disclosure. In some instances, the system 100 can be referenced as a therapeutic system, an ultrasound system, an ultrasound monitoring system, and/or combinations thereof. The system 100 includes a controller 108 in communication with an ultrasound system 106, a therapeutic device 110, and a vital sign monitoring device 112. The system 100 advantageously allows closed-loop control of the therapeutic device 110 based on ultrasound data. The system 100 also includes an ultrasound device 114 and a vital sign sensor 104 that obtains information about the medical status of the subject 102. In some circumstances, the system 100 may include additional elements and/or may be implemented without one or more of the elements illustrated in FIG. 1.

The ultrasound device 114 is sized and shaped, structurally arranged, and/or otherwise configured to be placed on or near the anatomy of the subject 102. The ultrasound device 114 obtains ultrasound data, which may be processed into an ultrasound image to visualize anatomy inside of the subject's body. The ultrasound device 114 may be positioned outside the body of the subject 102. In some embodiments, the ultrasound device 114 is positioned proximate to and/or in contact with the body of the subject 102. For example, the ultrasound device 114 may be placed directly on the body of the subject 102 and/or adjacent to the body of the subject 102. In that regard, the ultrasound device 114 includes a transducer array 115 which may be placed directly on or adjacent to the body of the subject 102. For example, a housing or lens of the ultrasound device 114 is placed directly in contact with the body of the subject 102 such that the transducer array 115 is adjacent to the body of the subject 102. The subject 102 may be a human patient or animal. The view of the anatomy shown in the ultrasound image depends on the position and orientation of the ultrasound device 114. To obtain ultrasound data of the anatomy, the ultrasound device 114 can be suitably positioned and oriented by a user, such as a medical doctor or a medical technician, so that the transducer array 115 emits ultrasound waves and receives ultrasound echoes from the appropriate portion of the anatomy. The ultrasound device 114 may be portable and suitable for use in a medical setting. In some instances, the ultrasound device 114 can be referenced as an ultrasound imaging device, a diagnostic imaging device, or combinations thereof.

The ultrasound device 114 can an external probe (e.g., a transthoracic echocardiography probe or TTE) with a housing sized and shaped for grasping by a user's hand and positioned outside of the subject's body. In some instances, the external ultrasound probe 114 is coupled to a mechanical arm or holder so that the probe 114 is positioned against the patient's skin. In some embodiments, ultrasound device 114 could also be a wearable patch that is positioned outside of the body and removably affixed to the body. Examples of skin mounted devices are described in U.S. Provisional App. No. 60/827,476, filed Sep. 29, 2006, the entirety of which is incorporated by reference herein.

In some embodiments, the probe 114 need not be held in the hand of a user. That is, the probe 114 can be positioned in the mechanical arm or be affixed to the patient such that ultrasound data can be acquired continuously or at regular or irregular time intervals before, during, and/or after a therapeutic procedure. This advantageously avoids the need for a human user to continuously maintain the probe 114 in position during the procedure. In some instances, the mechanical arm can be automatically adjusted (e.g., repositioned) in response to control signals sent by the ultrasound system 106 and/or the controller 108 to make sure the desired area of the anatomy is being interrogated. For example, if the patient moves during the procedure, the mechanical arm can adjust the orientation and/or positioning of the probe 114 to maintain the desired view. The wearable patch 114 is advantageously affixed to the patient so that it moves along with the patient's movements and thus maintains its view of the desired anatomy. In some instances, electronic beam steering is used in lieu of or in addition to physically moving the probe 114 to obtain ultrasound data from the desired anatomy.

In some embodiments, ultrasound device 114 can be an intraluminal device that is inserted into a body lumen of the subject's body. For example, the gastroscope of a transesophageal echocardiography (TEE) probe can inserted into the patient's esophagus to obtain ultrasound images of the patient's heart. The intraluminal device 114 can be a catheter or a guidewire in some instances, such as an intracardiac echocardiography (ICE) catheter or an intravascular ultrasound (IVUS) catheter.

The ultrasound device 114 is configured to obtain ultrasound imaging data associated with any suitable anatomy of the patient. For example, the ultrasound device 114 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, and/or other systems of the body. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the ultrasound device 114 may be used to examine man-made structures such as, but without limitation, heart valves, stents, shunts, filters, implants and other devices.

The transducer array 115 can be coupled at a distal portion of a probe 114 that is in contact with the subject's body. In some embodiments, the transducer array 115 can form part of the surface of the wearable patch 114 that is in contact with the subject's body. In some embodiments, the transducer array 115 can be coupled to distal portion of a gastroscope or a catheter in an intraluminal device 114.

The ultrasound transducer elements of the transducer array 115 are configured to emit ultrasound signals and receive ultrasound echo signals corresponding to the emitted ultrasound signals. The ultrasound echo signals may be processed by the ultrasound device 114 and/or in the ultrasound system 106. The transducer array 115 can be part of an imaging assembly, including an acoustic lens and a matching material on a transmitting side of the transducer array 115, and an acoustic backing material on a backside of the transducer array 115. The transducer array 115 may include any number of transducer elements. For example, the array can include between 1 acoustic element and 10000 acoustic elements, including values such as 2 acoustic elements, 4 acoustic elements, 15 acoustic elements, 64 acoustic elements, 128 acoustic elements, 500 acoustic elements, 812 acoustic elements, 3000 acoustic elements, 9000 acoustic elements, and/or other values both larger and smaller. The transducer elements of the transducer array 115 may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The transducer array 115 can be configured to obtain one-dimensional, two-dimensional, and/or three-dimensional images of patient anatomy. The ultrasound transducer elements may be piezoelectric/piezoresistive elements, piezoelectric micromachined ultrasound transducer (PMUT) elements, capacitive micromachined ultrasound transducer (CMUT) elements, and/or any other suitable type of ultrasound transducer elements.

The ultrasound transducer elements of the transducer array 115 are in communication with (e.g., electrically coupled to) the electronic circuitry of the ultrasound device 114. The electronic circuitry can be any suitable passive or active electronic components, including integrated circuits (ICs), for controlling the transducer array 115 to obtain ultrasound imaging data and/or processing the obtained ultrasound imaging data. For example, the electronic circuitry can include one or more transducer control logic dies. The electronic circuitry can include one or more application specific integrated circuits (ASICs). In some embodiments, one or more of the ICs can comprise a microbeamformer (μBF), an acquisition controller, a transceiver, a power circuit, a multiplexer circuit (MUX), etc. In some embodiments, the electronic circuity can include a processor, a memory, a gyroscope, and/or an accelerometer.

While only one ultrasound device 114 is illustrated in FIG. 1, it is understood that the system 100 can include two, three, four or more ultrasound devices 114. In that regard, the different ultrasound devices 114 can be configured to obtain ultrasound data of different anatomy of the subject 102. For example, one ultrasound device can monitor a left lung and another ultrasound device can monitor a right lung. As described herein, the ultrasound data obtained by the multiple devices 114 can be used by the controller 108 to provide closed-loop of the therapeutic device 110.

The ultrasound system 106 is in communication with the ultrasound device 114. In that regard, the ultrasound device 114 can be electrically and/or mechanically coupled to the ultrasound system 106. For example, the ultrasound device 114 can be in wired or wireless communication with the ultrasound system 106. In some embodiments, the system 100 omits the ultrasound system 106, and the ultrasound device 114 is communication with the controller 108.

The ultrasound system 106 can be a console in some instances. The ultrasound system 106 could be a movable cart, a mobile device (e.g., a smart phone, a tablet, a laptop, or a personal digital assistant or PDA) with integrated processor(s), memory, and display. The ultrasound system 106 can include a user interface 122 and a display 123. The ultrasound system 106 also includes processing circuitry (e.g., one or more processors in communication with memory) configured to control acquisition of the ultrasound data by the ultrasound device 114 and to process the obtained ultrasound data. In some instances, the obtained ultrasound data is imaging data that the ultrasound system 106 processes to generate an ultrasound image and output the ultrasound image on the display 123. The ultrasound system 106 processes the ultrasound data obtained by device 114 to extract information about the anatomy of the patient (e.g., measurements of anatomy, ultrasound features), including the effect the therapy on the subject's anatomy. The anatomical information can be extracted from the ultrasound data with or without generating an ultrasound image for display. A user can control various aspects of acquiring ultrasound imaging data by the ultrasound device 114 and/or viewing of ultrasound images on the display 123 by providing inputs at the user interface 122. The ultrasound device 114 and display 123 may be communicatively coupled directly or indirectly to the ultrasound system 106. In embodiments in which the system 106 is a mobile device, the integrated touchscreen can be the user interface 122 and the display 123. In embodiments that omit the ultrasound system 106, the processing can be performed by processing circuitry (e.g., one or more processors in communication with memory) in the ultrasound device 114.

The system 100 includes vital sign sensor 104. While sensor 104 can be described as a vital sign sensor in some embodiments, it is understood that the sensor 104 can be any suitable sensor that obtains physiological information about the subject's anatomy, including the effect the therapy on the subject's anatomy. The sensor 104 is sized and shaped, structurally arranged, and/or otherwise configured to be placed inside, on, or near the anatomy of a subject 102 to obtain physiological information about the subject's body. The sensor 104 can be a pressure sensor, a temperature sensor, pulse rate sensor, respiration sensor, electrocardiogram (ECG) probe and/or electrode patch, pulse oximetry sensor, arterial pressure sensor, glucose sensor, a non-imaging flow sensor, bioimpedance sensor, a hydration sensor, other suitable sensors, and/or combinations thereof. For example, the sensor 104 can be a combination of two or more sensors (e.g., the same component performs as two or more sensors and/or two or more sensors are integrated in a single housing). The sensor 104 can provide invasive or noninvasive monitoring of the subject's medical condition. While only one vital sign sensor 104 is illustrated in FIG. 1, it should be understood that the system 100 may include any number of vital sign sensors, include one, two, three, four, or more. An advantageous feature of the present disclosure is closed-loop control of the therapeutic device 110 based on the data obtained by one or more vital sign sensor 104 and/or one or more ultrasound devices 114 monitoring the subject 102 simultaneously and in real-time. For example, the one or more sensors 104 can be attached to the skin of the body of the subject 102. The sensor 104 can be attached to the skin of the subject 102, inserted into the body, and/or otherwise affixed to the inside or the outside of the body (e.g., sensor straps, strapping tape, etc.).

The vital sign sensor 104 is in communication with the vital sign monitoring device 112. The vital signal monitoring device 112 can be a console associated with the vital sign sensor 104. In that regard, the monitoring device 112 can include processing circuitry (e.g., one or more processors in communication with memory) that receives, interprets, and/or processes the data received from the sensor 104 such that the electrical, optical, pressure, and/or other signals from the sensor 104 can output as values of measure physiology quantity. The vital sign sensor 104 can be in wired or wireless communication with the vital sign monitoring device. The vital sign monitoring device 112 is helps provide additional information to the medical and nursing staff about the physiologic condition of the subject 102.

The therapeutic device 110 of the system 100 provides therapy to the subject 102. In that regard, the therapeutic device 110 can be in fluid communication with body of the subject 102 via e.g., tubes or conduits that allow for transmission of fluid. The therapeutic device 110 could be any medical device that prevents, diagnoses, monitor, alleviate, treat, cure, or compensate for, a disease, ailment, defect, or injury. In some embodiments, the therapy device 110 could be influencing, inhibiting, or modifying a physiological process, testing the susceptibility of person to a disease or ailment, investigating, replacing, or modifying parts of the human anatomy.

For example, the therapeutic device 110 can be any hemodynamic therapy and/or hemodynamic monitoring device. These hemodynamic devices may include an infusion device, a ventilator, and a dialysis machine. A dialysis machine is used to filter a patient's blood to remove excess water and waste products when the kidneys are damaged, dysfunctional, or missing. The dialysis machine itself can be thought of as an artificial kidney. The dialysis machine can provide therapy to the patient using intravenous (IV) access, such as with a catheter, tube, line, etc. A medical or mechanical ventilator is a machine designed to move breathable air into and out of the lungs, to provide breathing for a patient who is physically unable to breathe or breathing insufficiently. The dialysis machine can provide therapy to the patient using a tube that allows air, oxygen, and/or carbon dioxide to pass between the machine and the patient's lungs. An infusion system is used to deliver infusions while protecting each patient. For example, an infusion pump infuses fluids, medication or nutrients into a patient's circulatory system. It is generally used intravenously, although subcutaneous, arterial and epidural infusions can be used. The infusion system can provide therapy to the patient using intravenous (IV) access, such as with a catheter, tube, line, etc.

The therapeutic device 110 can include processing circuitry (e.g., one or more processors in communication with memory) to control delivery of therapy to the subject 102. In that regard, the operating status of the therapy device 110 can be defined by one or more adjustable parameters. The parameters can be discrete values (e.g., on/off, low/high/medium, etc.) and/or continuous values (e.g., numerical quantities). For example, operating status of the dialysis machine can be defined by an on/off status, inflow rate, outflow rate, filtration rate, amount of fluid to be removed, other suitable parameters, and/or combinations thereof. For example, the operating status of the ventilator can be defined by an on/off status, oxygen percentage, pressure, volume, flow, tidal volume, respiration rate, positive end expiratory pressure (PEEP), fraction of inspired oxygen ($FiO_2$) settings, other suitable parameters, and/or combinations thereof. For example, the operating status of the infusion system can be defined by an on/off status, flow rate, infusion rate, total volume of infusion, other suitable parameters, and/or combinations thereof.

The system 100 includes the controller 108 directly or indirectly in communication with the ultrasound device 114, the ultrasound system 106, the vital sign sensor 104, the vital sign monitoring device 112, and/or the therapeutic device 110. In general, the controller 108 is configured to receive ultrasound data and/or vital sign data, determine how a patient's therapy is progressing based on the received data, and output a control signal to the therapeutic device 110 to change its operating status. In this manner, the controller 108 provides closed loop control of the therapeutic device 110 based on the received ultrasound data and/or vital sign data. The controller 108 advantageously increases the robustness of patient therapy by repeatedly and/or continuously monitoring the patient's response to the therapy in real-time and in response, adjusting the therapy in real-time.

The controller 108 can include processing circuitry, such as one or more processors 116 in communication with memory 118. The processor 116 may be an application-specific integrated circuit (ASIC), a field-programmable gate array (FPGA), a central processing unit (CPU), a digital signal processor (DSP), another hardware device, a firmware device, or any combination thereof configured to perform the operations described herein. In some embodiments, the memory 118 is a random access memory (RAM). In other embodiments, the memory 118 is a cache memory (e.g., a cache memory of the processor), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory 118 may include a non-transitory computer-readable medium. The memory 118 may store instructions that, when executed by the processor 116, cause the processor 116 to perform operations described herein in connection with embodiments of the present disclosure. In that regard, processing steps described herein can be carried out by the controller 108. In some embodiments, the controller 108 may include a database for holding and storing the collected and the computed data, e.g., for later use in addition to the real-time use discussed herein.

The controller 108 can be in communication with a display 120, which is an output device for presentation of information in visual or tactile form. In some embodiments, the controller 108 can output display data based on the receiving ultrasound and/or vital sign data, processing the data, and generating the control signal(s) for the therapeutic device 110. In some embodiments, the display 120 can be television or computer monitor, or a touchscreen of a mobile device (e.g., a smart phone, a tablet, a laptop, or a personal digital assistant or PDA).

In some embodiments, the controller 108, the ultrasound device 114, the ultrasound system 106, the vital sign sensor 104, the vital sign monitoring device 112, the therapeutic device 110, and/or other components of the system 100 are individual units, e.g., with separate and distinct housing. It should be understood that the system 100 may include different configurations. For example, one or more of the components in the system 100 can be combined, e.g., within the same housing or attached housing. In some embodiments, the controller 108 may be implemented as part of the ultrasound system 106 or the therapeutic device 110. In some embodiments, both the controller 108 and the ultrasound system 106 are implemented in the ultrasound device 114. In some embodiments, the ultrasound device 114, the ultrasound system 106, the therapeutic device 110, the vital sign monitoring device 112, and/or the controller 108 may have their own individual processing circuitry and/or display. One or more of the components of the system 100 includes hardware and/or software to carry out the steps described herein. In some embodiments, the ultrasound device 114, the ultrasound system 106, the therapeutic device 110, the vital sign monitoring device 112, and/or the controller 108 share processing circuitry and/or display. In some instances, one or more components of the system 100 are implemented as a console, a table top device, a bedside device, and/or a mobile device.

Any suitable wired or wireless communication can be implemented between components of the system 100. For example, the ultrasound device 114 can operates wirelessly when communicating with the cooperating components of the system 100, such as the ultrasound system 106, the controller 108, the therapeutic device 110, and/or the vital signal monitoring device 112. For example, the wireless connection can be between the ultrasound device 114 and the controlled therapeutic device 110 and/or between one or more components of the system 100 and a local area network. For example, an authorized computer with access to the local area network can be alerted for some action taken in the system 100.

Figure 2:
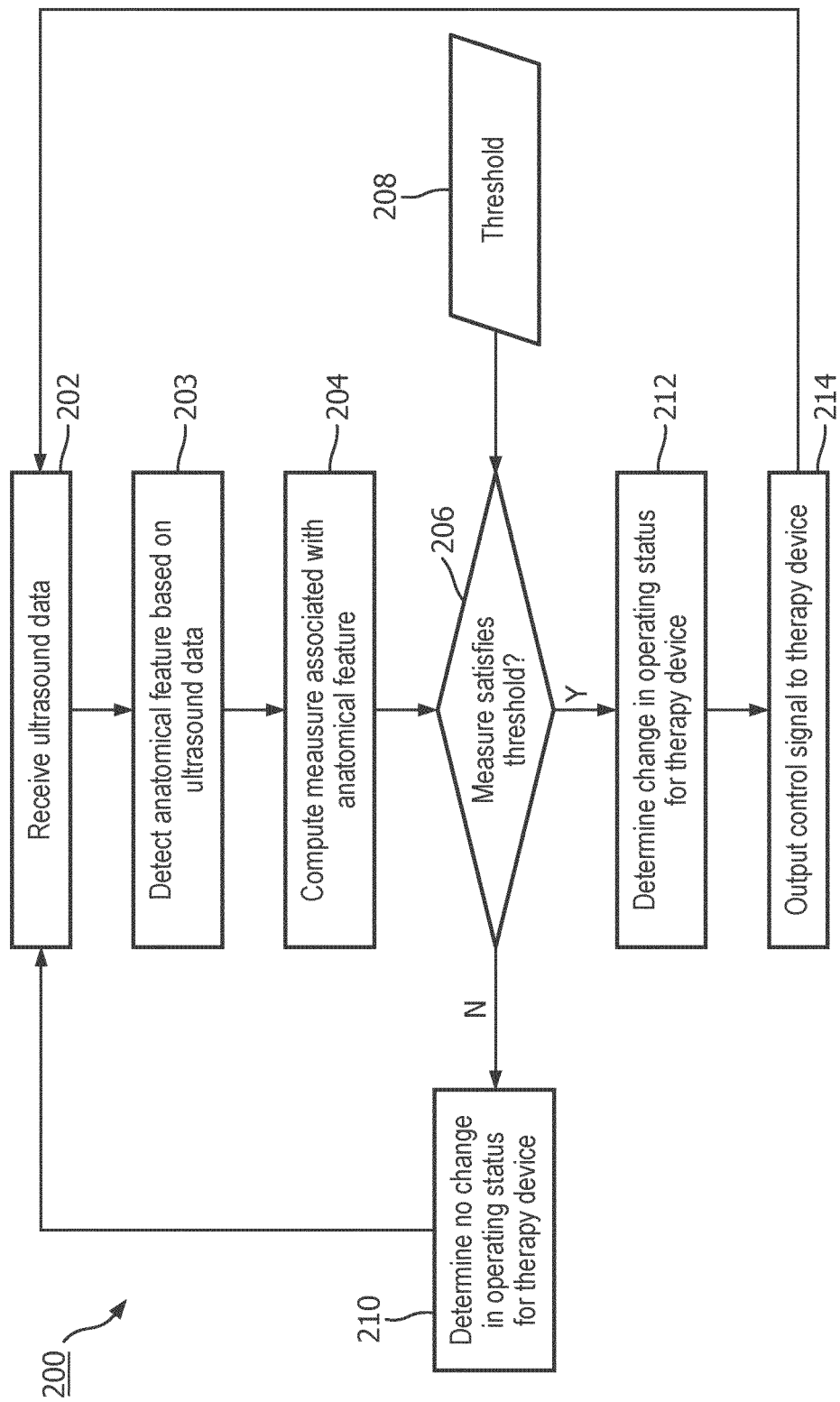
FIG. 2 is flow diagram of a method for closed loop control of a therapeutic device using ultrasound data, according to aspects of the present disclosure.

FIG. 2 is a flow diagram of a method 200 for closed-loop control of a therapeutic device using ultrasound data, according to aspects of the present disclosure. In that regard, the steps of the method 200 can be carried in an automated manner, without user intervention, to control operation of the therapeutic device 110.

At step 202, the method 200 includes receiving ultrasound data. For example, the ultrasound device 114 can be activated to scan the subject 102. Step 202 can include the transducer array 115 receiving the ultrasound echoes from the subject's anatomy, the ultrasound system 106 receiving the ultrasound data from the ultrasound device 114, and/or the controller 108 receiving the ultrasound data from the ultrasound device 114 and/or the ultrasound system 106. Any suitable ultrasound data is contemplated including imaging data, 2D data, 3D data, B-mode data, flow data, Doppler data, etc.

At step 203, the method 200 includes detecting one or more anatomical feature(s) based on the received ultrasound data. For example, the ultrasound data can be processed by the ultrasound system 106 and/or the controller 108 to extract anatomical features. The anatomical feature can be a structure (e.g., all or a portion of an organ) within a body of the subject 102, an indication of a healthy or diseased physiology, indications of functionality of one or more systems of the body, etc. In some embodiments, the anatomical features can be detected by the controller 108 based on the visualization of the anatomy with the ultrasound data. In some embodiments, the anatomical features can be detected by the ultrasound system 106 and/or controller 108 based on features of the ultrasound data itself. In an exemplary embodiment, the anatomical feature is the presence of a pulmonary edema, which is determined based on the identification of B-lines (e.g., reverberation artifacts that manifest in an ultrasound image of the lung) in the ultrasound data. In other exemplary embodiments, the anatomical feature is the left ventricle (LV), the right ventricle (RV), and/or the inferior vena cava (IVC).

At step 204, the method 200 includes computing one or more measure(s) associated with the detected anatomical feature. Generally, the measure may be a numerical quantity that is representative of the health of the subject 102. For example, the measure itself and/or the change in the measure over time is indicative of the response of the subject 102 to the therapy. In exemplary embodiments, the measure can be a geometrical description of the anatomy, such as an area, volume, diameter, length. For example, the ultrasound system 106 and/or the controller 108 can calculate a diameter of the IVC, a volume of the LV, a volume of the RV, and/or other suitable quantities. In some embodiments, the measure can be quantification of attributes of the ultrasound data, such as a quantity of B-lines. For example, a larger number of B-lines can be indicative of a more severe pulmonary edema and a fewer number of B-lines can be indicative of less severe pulmonary edema.

At step 206, the method 200 includes evaluating whether the computed measure satisfies one or more threshold(s). In that regard, the controller 108 can receive a threshold 208 that represents a desired or intended value of the measure as a result of the therapy. For example, the threshold represents what value of the computed measure should be if the therapy is successful or proceeding satisfactorily. In that regard, the threshold 208 can be multiple values, such as different values for the measure at different times after start of the procedure. For example, the controller 108 can be configured with threshold values expected any suitable time intervals, such as after 30 minutes of therapy, after 1 hour of therapy, after 1.5 hours of therapy, etc. By comparing the computed measure (step 204) with the threshold 208 in step 208, the controller 108 determines how well the subject 102 is responding to the therapy. In different embodiments, satisfaction of the threshold can include the computed measure (step 204) being greater than or less than the threshold 208. The threshold 208 can be based on literature values or values specific to the subject 102. The threshold 208 can be manually inputted by a user to the controller 108 and/or calculated by the controller 108.

If the measure satisfies the threshold in step 206, then at step 212, the method 200 includes determining a change in the operating status of the therapeutic device. For example, in some embodiments, satisfaction of the threshold indicates that therapy is proceeding satisfactorily and/or that the therapy is successful. That is, the subject 102 is responding well to the therapy such that the response is indicated in the anatomical feature (step 203) and computed measure (step 204). Accordingly, the controller 108 can determine a modification to the operation of the therapeutic device 110 to maintain the good progress of the therapy. For example, the change in operating status of the therapy device 110 could include turning the device off, for example, if the comparison (step 206) indicates that the desired effect of the therapy has been realized. In general, the change in operating status of the therapy device 110 can be turning the device off or on, putting the device into standby, waking the device from standby, etc. In some instances, when the comparison (step 206) indicates that the therapy is progressing as desired but not yet complete, the therapy device may be changed from high or medium setting to a low setting because the intensity of the therapy at the middle or later stages of the therapy need not be as high as it was at the beginning. Generally, an operating parameter of the therapy device 110 can be changed from one setting (e.g., low, medium, or high) to another setting. In some instances, the change in the operating status can be an increase or decrease in the value of an operating parameter, e.g., the amount of medicine that is being delivered to the subject 102.

At step 214, the method 200 outputs a control signal to the therapeutic device that is representative of the determined change. In that regard, the controller can generate and transmit the control signal to the therapeutic device to change its operation. In this manner, the controller 108 advantageously provides closed-loop control of the therapy device.

If the measure does not satisfy the threshold in step 206, then at step 212, the method 200 includes determining no change in the operating status of the therapy device. For example, the comparison (step 206) can indicate that the therapy has not achieved the degree of expected benefit yet. Accordingly, the controller 108 can determine that the existing operating parameters of the therapy device 110 should continue. In that regard, the existing operating parameters can be automatically determined by an earlier iteration of the method 200 or manually by a clinician. In such embodiments, the controller 108 does not send any control signal to the therapy device 110 when not change in operating status is needed. In other embodiments, the controller 108 sends a control signal with operating parameters identical to the existing operating parameters, such that there is no change in the therapy.

It is understood that the method 200 can include steps opposite to those shown in FIG. 2 based on the comparison (step 206) between the computed measure (step 204) and the threshold 208. For example, the controller 108 can determine the change in operating status for the therapeutic device 110 (step 212) when the computed measure does not satisfy the threshold. In that situation, for example, the controller 108 determines that the subject 102 is not responding to the therapy as desired, and the intensity of the therapy can be increased in order to bring about the desired therapeutic effect. Likewise, the controller 108 can determine that there does not need to be any change in the operating status for the therapeutic device 110 (step 210) when the measure satisfies the threshold. For example, if the therapy is progressing satisfactorily, then the therapeutic device 110 can continue with the existing parameters.

The method 200 can be repeated continuously or periodically. For example, after steps 210, 214, the method 200 can restart at the step 202. For example, the method 200 can be repeated at fixed or variable time intervals to monitor the progress of the therapy delivered to the subject 102 by the therapeutic device 110. In some embodiments, at the start of each iteration of the method 200, the controller 108 and/or the ultrasound system 106 initiates operation of the ultrasound device 114 to obtain ultrasound data.

The method 200 can include outputting an indication, e.g., to the display 120, representative of one or more operations. For example, the controller 108 can generate a visual representation of the result of the comparison (step 206) and/or the determined change in the operating status (step 212).

In an exemplary embodiment, the method 200 can be implemented in the context of controlling a dialysis machine using ultrasound data. For example, the patient is placed on a dialysis machine. Wearable ultrasound sensors are affixed on the patient chest so that ultrasound data of the lung is obtained. Lung ultrasound features, such as B-lines, indicate the presence of pulmonary edema. At periodic time intervals, such as every 15 minutes, the ultrasound system that operates the ultrasound sensors performs ultrasound imaging. The ultrasound system utilizes the ultrasound data to automatically identify the presence of B-lines. A measure of severity can be computed based on the quantity of B-lines, as described, for example, in U.S. Provisional App. No. 62/477,536, filed Mar. 28, 2017, the entirety of which is incorporated by reference herein. At the start of the dialysis, the patient's B-line score is expected to be high due to the presence of retained fluid in the body. The ultrasound system communicates with the controller, which evaluates whether a threshold criterion is met at each evaluation time interval. For example, the controller determines whether the B-line score has been reduced to a lower level, below the threshold. The controller also communicates with the dialysis machine.

Once the B-line severity score has sufficiently reduced, the controller turns off the dialysis machine. The controller can also output an indication of turning off the dialysis machine to the nurse or doctor.

In an exemplary embodiment, the method 200 can be implemented in the context of controlling infusion of medication using ultrasound data. In particular, the context can be for controlled infusion of medication and/or fluid for patients with impaired hemodynamic status in the intensive care unit. Exemplary medications include vasopressors that induce vasoconstriction or inotropes that increase cardiac contractility. One or more ultrasound devices (e.g., in-body TEE probes or wearable probes) are used to image the heart and/or the IVC (and its variations due to respiration) continuously or intermittently. The ultrasound system and/or the controller converts the ultrasound data into a measure of LV and RV volumes. The LV volume and/or RV volume can be representative of a measurement of cardiac output. Automated ultrasound to determine cardiac features is described in Otani et al., *Three-Dimensional Echocardiographic Assessment of Left Heart Chamber Size and Function with Fully Automated Quantification Software in Patients with Atrial Fibrillation,* Journal of the American Society of Echocardiography (Volume 29, Issue 10, October 2016, pages 955-965), the entirety of which is incorporated by reference herein. If the LV function, e.g., as determined by cardiac output measurement or LV volume, is lower than a threshold, then the controller adjusts an infusion device in order to increase the amount of inotropes. The controller also automatically computes IVC diameters to determine if the IVC is collapsed. Aspects of the present disclosure include features similar to those described in International Application No. PCT/CN2015/075831, filed Apr. 3, 2015, and titled "Fully automated user-independent identification and segmentation of the inferior vena cava," the entirety of which is incorporated by reference herein. If the IVC is collapsed as determined by comparison of the IVC diameter to the threshold, then the controller adjusts the infusion device in order to increase fluid administered to the patient.

Figure 3:
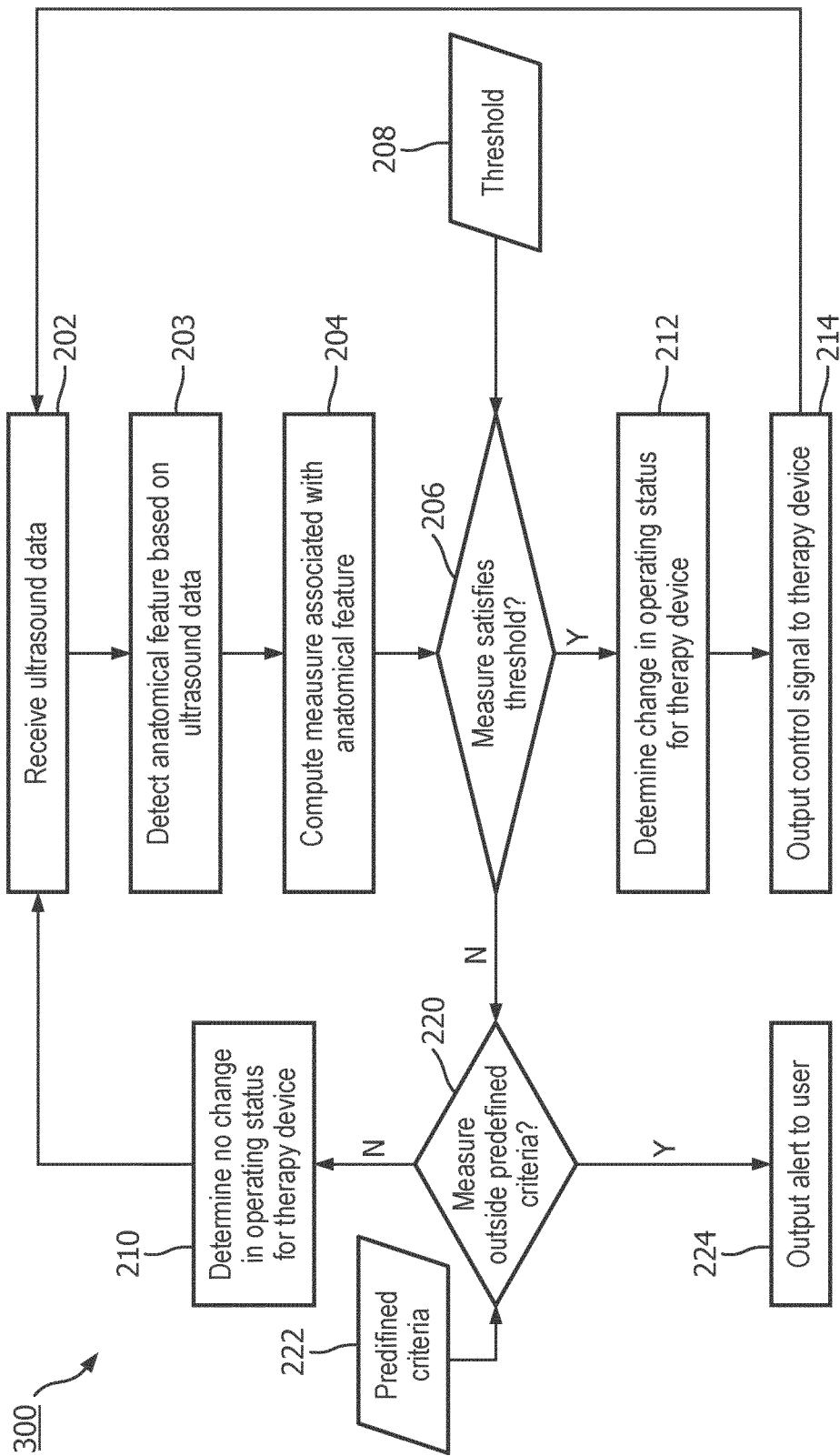
FIG. 3 is flow diagram of a method for closed loop control of a therapeutic device using ultrasound data, according to aspects of the present disclosure.

FIG. 3 is a flow diagram of a method 300 for closed-loop control of a therapeutic device using ultrasound data, according to aspects of the present disclosure. In that regard, the steps of the method 300 can be carried in an automated manner, without user intervention, to control operation of the therapeutic device 110.

The method 300 includes steps 202, 203, 204, 206, 208, 210, 212, and 214, similar to those described with respect to the method 200 (FIG. 2). The method 300 additionally alerts a user in case of detecting abnormal data during processing.

At step 220, the method 300 includes determining if the measure is outside of predefined criteria/criterion. For example, the controller 108 can receive the predefined criteria 222, which are representative of, e.g., upper and/or lower bounds for the measure that ensure patient safety. The predefined criteria 222 can be based on literature values or values specific to the subject 102. The predefined criteria 222 can be manually inputted by a user to the controller 108 and/or calculated by the controller 108. In that regard, the comparison (step 220) can be indicative of when automated control of the therapeutic device 110 may no longer be helpful to the patient so that a human user, such as a doctor, is alerted. For example, the controller 108 can determine if the computed measure (step 204) falls outside of the expected values (e.g., the computed measure is greater than an upper bound or less than a lower bound). Such values can be indicative that the therapy is ineffective and should not be continued, for example.

In the illustrated embodiment of FIG. 3, the comparison between the computed measure and the predefined criteria (step 220) occurs after determining that the measure does not satisfy the threshold 208 (step 206). In other embodiments, step 220 can be performed before or in parallel with the step 206, or after determining that the measure does satisfy the threshold.

Step 220 generally represents comparison of any quantity associated with the therapy (not just the computed measure of step 204) to predefined criteria (e.g., upper and/or lower bounds) to ensure patient safety. For example, the duration of the therapy can be compared to maximum duration to ensure that therapy is not dangerously prolonged. For example, the volume or volume per unit time of medication can be compared corresponding maximum criteria to ensure that too much medication is not administered.

At step 224, when the computed measure falls outside of the predefined criteria, the method 300 includes outputting an alert to the user. For example, the controller 108 can output the alert to a user in a graphical format on the display 120. In some instances, the alert includes an audible component. A monitoring user may gain access to alert via a host terminal, which may be directly connected to the controller 108 or may be connected via a computer network, such as the Internet. In one such embodiment, the alert provided by the controller 108 may be transmitted to the host terminal as data via the Internet or any type of data or computer network. The alert may then be displayed to the user on the host terminal using a graphical user interface (GUI). As the information regarding the patient current health condition and therapy are displayed on the GUI, the user may then interact with that information using the GUI. In response to the alert, the user can stop the therapy and/or initiate new, different therapy. In some situations, the doctor can choose to continue the therapy within the purview of her expertise, given the particular health conditions of the subject 102.

When the computed measure falls outside of the predefined criteria, the method 300 continues with determining that no change is required in the operating status of the therapeutic device 110, as described with response to method 200 (FIG. 2).

Figure 4:
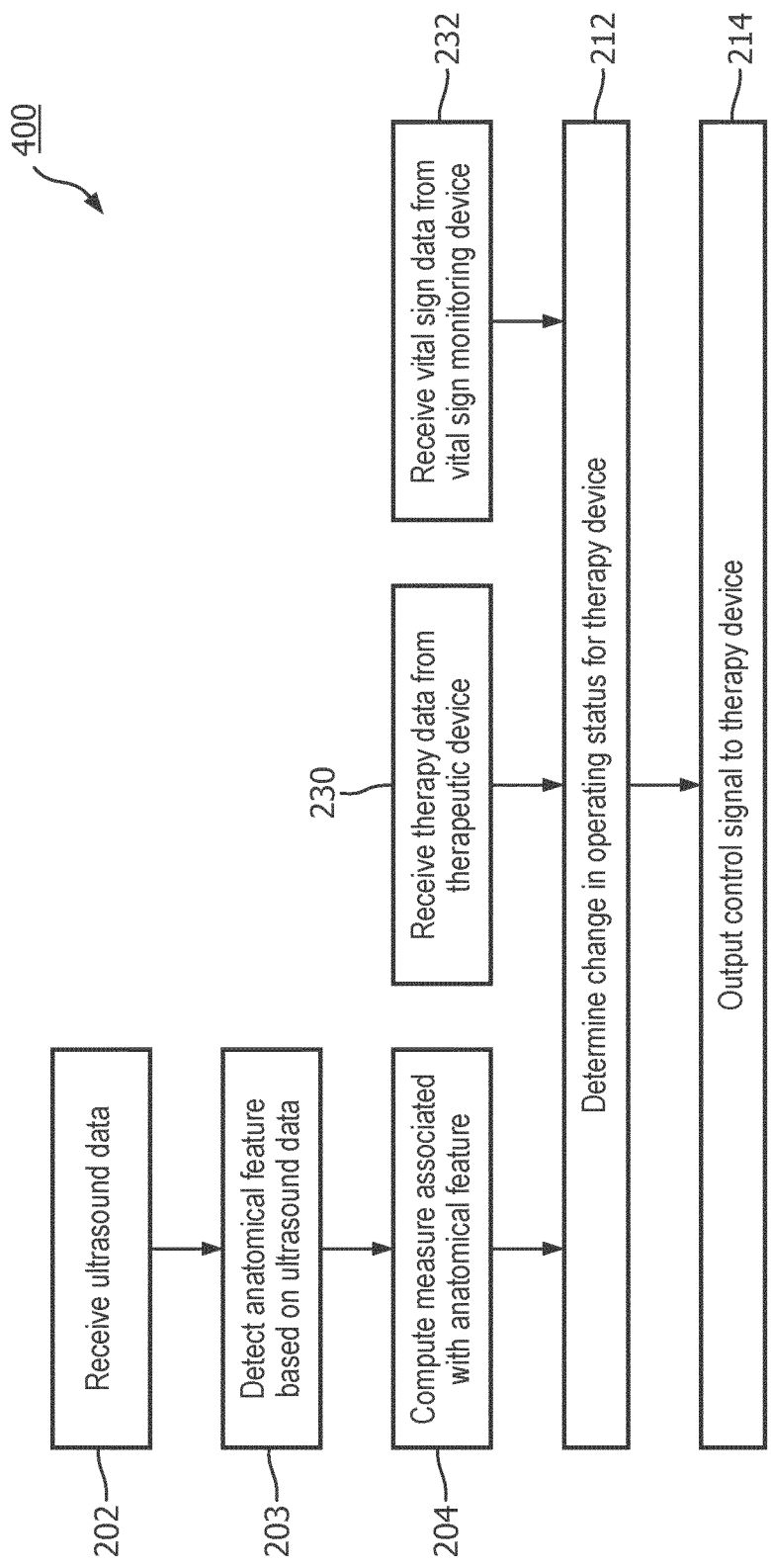
FIG. 4 is flow diagram of a method for closed loop control of a therapeutic device using ultrasound data, according to aspects of the present disclosure.

FIG. 4 is a flow diagram of a method 400 for closed-loop control of a therapeutic device using ultrasound data, according to aspects of the present disclosure. In that regard, the steps of the method 400 can be carried in an automated manner, without user intervention, to control operation of the therapeutic device 110.

The method 400 includes steps 202, 203, 204, 212, and 214, similar to those described with respect to the method 200 (FIG. 2). The method 400 can also include steps 206, 208, and/or 210 of the method 200 (FIG. 2). The method 400 additionally utilizes data from the therapeutic device 110 and/or the vital sign monitoring device to determine the change in the operating status for the therapeutic device 110.

At step 230, the method 400 includes receiving therapy data from the therapeutic device. For example, the controller 108 receives data from the therapeutic device 110, including the current operating parameters, the elapsed time of the therapy, instantaneous and/or average values of one or more parameters (e.g., on/off status, inflow rate, outflow rate, filtration rate, amount of fluid removed, amount of fluid yet to be removed, oxygen percentage, pressure, volume, flow, tidal volume, respiration rate, positive end expiratory pressure (PEEP), and/or fraction of inspired oxygen ($FiO_2$) settings, flow rate, infusion rate, total volume of infusion, other suitable values and/or combinations thereof)

At step 232, the method 400 includes receiving vital sign data from the vital sign monitoring device. For example, the controller 108 receives the vital sign data from the vital sign monitoring device 112 and/or the vital sign sensor 104. Exemplary vital sign data can include as ECG data, pulse oximetry data, arterial pressure data.

At step 212, the method 400 can utilize the computed measure (step 204) from the ultrasound data, the therapy data (step 230), and/or the vital sign data (step 232) in determining the change in operating status. In some embodiments, step 212 include implement multi-parameter model to take the multiple types of data into consideration in determining if and how the operating status of the therapy device should be change. The multi-parameter model can include weighted averages, repeated random sampling to obtain numerical results such as Monte Carlo, machine learning approaches, and/or any other suitable computational approach.

As illustrated in FIGS. 2, 3, and 4, the methods 200, 300, 400 include a number of enumerated steps, but embodiments of the methods 200, 300, 400 may include additional steps before, after, and in between the enumerated steps. In some embodiments, one or more of the enumerated steps may be omitted, performed in a different order, or performed concurrently. The steps of the methods 200, 300, 400 can be carried by the controller 108. In some embodiments, some steps of the methods 200, 300, 400 can be carried out by the ultrasound system 106 and/or the ultrasound device 114.

Advantageously, this invention provides a closed-loop control system for control of the therapeutic device 110. The disclosed principles provide for algorithms that use the data from the one or more sensors and probes to create a robust therapy model that will evaluate and maintain the health of the patient. The closed-loop control system obtains data from the patient and alters the therapy automatically without human intervention, which addresses open-loop systems that lead to sub-optimal patient treatment. Aspects of the present disclosure can be applied in all locations where patient monitoring needs to be done. Patient monitoring includes the emergency rooms (ER), intensive care unit (ICU), ward, dialysis centers, or out-of-hospital environments.

What is claimed is:

1. A system, comprising:
  a transducer array configured to obtain ultrasound data of a subject, wherein the transducer array comprises a plurality of transducers and wherein the ultrasound data is imaging data;
  a therapeutic device configured to deliver a therapy to the subject; and
  a processor in communication with the transducer array and the therapeutic device, wherein the processor is configured to:
    receive the ultrasound data;
    identify an anatomical feature of the subject using the ultrasound data;
    compute a measure associated with the anatomical feature;
    determine if the measure satisfies a threshold;
    determine a change in an operating status of the therapeutic device based on if the measure satisfies the threshold;
    output, to the therapeutic device, a control signal representative of the change in the operating status; and
    change the operating status of the therapeutic device based on the control signal.

2. The system of claim 1, wherein:
  the operating status of the therapeutic device comprises an on/off status of the therapeutic device; and
  the change in the operating status of the therapeutic device based on the control signal comprises turning the therapeutic device on or off.

3. The system of claim 1, wherein;
  the operating status of the therapeutic device comprises an adjustable parameter of the therapeutic device; and
  the change in the operating status of the therapeutic device based on the control signal comprises an increase or a decrease in a value of the adjustable parameter.

4. The system of claim 1, wherein:
  the anatomical feature is a pulmonary edema;
  the ultrasound data comprises B-lines; and
  the measure comprises a quantity of the B-lines.

5. The system of claim 1, wherein:
  the anatomical feature comprises an inferior vena cava; and
  the measure comprises a diameter of the inferior vena cava.

6. The system of claim 1, wherein:
  the anatomical feature comprises at least one of a right ventricle or a left ventricle; and
  the measure comprises a volume of at least one of the right ventricle or the left ventricle.

7. The system of claim 1, wherein the therapeutic device comprises at least one of a dialysis machine, an infusion device, or a ventilator.

8. The system of claim 1, wherein the processor is configured to:
  determine if the measure is outside of a predefined criteria; and
  output an alert to a user based on determining if the measure is outside of the predefined criteria.

9. The system of claim 8, wherein:
  the processor is in communication with a display; and
  the processor outputting the alert comprises providing a graphical representation of the alert to the display.

10. The system of claim 1, wherein:
  the processor is configured to receive therapy data from the therapeutic device; and
  the processor determining the change in the operating status of the therapeutic device is further based on the therapy data.

11. The system of claim 1, wherein:
  the processor is in communication with a vital sign monitoring device;
  the processor is configured to receive vital sign data from the vital sign monitoring device; and
  the processor determining the change in the operating status of the therapeutic device is further based on the vital sign data.

12. The system of claim 1, further comprising:
  at least one of a transthoracic echocardiography (TTE) probe, a transesophageal echocardiography probe (TEE), or a wearable patch, wherein the transducer array is coupled to at least one of the TTE probe, the TEE probe, or the wearable patch.

13. The system of claim 1, wherein the anatomical feature comprises one or more of a structure within a body of the subject, an indication of a healthy or diseased physiology, or an indication of functionality a systems of the body.

14. The system of claim 1, wherein the measure comprises a numerical quantity that is indicative of a response of the subject to the therapy, wherein the numerical quantity comprises:
- a geometrical description of the anatomical feature, wherein the geometrical description comprises an area, a volume, a diameter, a length, or a combination thereof;
- a quantification of attributes of the ultrasound data; or
- a combination thereof.

15. The system of claim 1, wherein the threshold represents a desired or intended value of the measure as a result of the therapy, and the threshold comprises multiple values, the threshold value changes over time, or a combination thereof.

16. A method, comprising:
- delivering therapy to a subject with a therapeutic device;
- receiving ultrasound data of a subject obtained by a transducer array, wherein the transducer array comprises a plurality of transducers and wherein the ultrasound data is imaging data;
- identifying, by a processor in communication with the transducer array, an anatomical feature of the subject using the ultrasound data;
- computing, by the processor, a measure associated with the anatomical feature;
  - determining, by the processor, if the measure satisfies a threshold;
- determining, by the processor, a change in an operating status of the therapeutic device based on if the measure satisfies the threshold;
- outputting, by the processor, a control signal representative of the change in the operating status to the therapeutic device;
- receiving, by the therapeutic device, the control signal; and
- changing automatically the operating status of the therapeutic device based on the control signal.

17. The method of claim 16, wherein:
the operating status of the therapeutic device comprises an on/off status of the therapeutic device; and
changing automatically the operating status of the therapeutic device based on the control signal comprises turning the therapeutic device on or off.

18. The method of claim 16, wherein:
the operating status of the therapeutic device comprises an adjustable parameter of the therapeutic device; and
changing automatically the operating status of the therapeutic device based on the control signal comprises increasing or decreasing a value of the adjustable parameter.

19. The method of claim 16, further comprising:
- determining if the measure is outside of a predefined criteria; and
- outputting an alert to a user based on determining if the measure is outside of the predefined criteria.

20. The method of claim 16, wherein determining the change in the operating status of the therapeutic device is further based on the therapy data.

21. The method of claim 16, further comprising receiving vital sign data of the subject from a vital sign monitoring device; wherein determining the change in the operating status of the therapeutic device is further based on the vital sign data.

* * * * *